(12) United States Patent
Schmidt et al.

(10) Patent No.: US 9,714,996 B2
(45) Date of Patent: Jul. 25, 2017

(54) ESTABLISHING $B_1$-MAPS (71) Applicants: Andreas Schmidt, Erlangen (DE);
Thorsten Speckner, Erlangen (DE);
Johann Sukkau, Herzogenaurach (DE);
Michael Wullenweber, Erlangen (DE)

(72) Inventors: Andreas Schmidt, Erlangen (DE);
Thorsten Speckner, Erlangen (DE);
Johann Sukkau, Herzogenaurach (DE);
Michael Wullenweber, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 485 days.

(21) Appl. No.: 14/481,696

(22) Filed: Sep. 9, 2014

(65) Prior Publication Data
US 2015/0070013 A1 Mar. 12, 2015

(30) Foreign Application Priority Data

Sep. 11, 2013 (DE) .......................... 10 2013 218 224

(51) Int. Cl.
*G01V 3/00* (2006.01)
*G01R 33/54* (2006.01)
(Continued)

(52) U.S. Cl.
CPC ........... *G01R 33/54* (2013.01); *G01R 33/246* (2013.01); *A61B 5/055* (2013.01); *G01R 33/5612* (2013.01); *G01R 33/5659* (2013.01)

(58) Field of Classification Search
USPC ....................................................... 324/309
See application file for complete search history.

(56) References Cited

U.S. PATENT DOCUMENTS

| 2008/0100292 | A1 | 5/2008 | Hancu |
| 2011/0115483 | A1* | 5/2011 | Zhai .................... G01R 33/5659 324/307 |

(Continued)

FOREIGN PATENT DOCUMENTS

| DE | 102010013672 A1 | 10/2011 |
| DE | 102012203453 A1 | 9/2013 |

OTHER PUBLICATIONS

German Office Action dated Jun. 23, 2014 for corresponding German Patent Application No. DE 10 2013 218 224.4 with English translation.
P-F. Van de Moortele, et al., "Calibration Tools for RF Shim at Very High Field with Multiple Element RF Coils: from Ultra Fast Local Relative Phase to Absolute Magnitude B1+Mapping," Proc. Intl. Soc. Mag. Reson. Med. 15, p. 1676, (2007).

*Primary Examiner* — Rodney Fuller
(74) *Attorney, Agent, or Firm* — Lempia Summerfield Katz LLC (57) ABSTRACT

The embodiments relate to a $B_1$-map establishment system for establishing $B_1$-maps, operating using a method including: establishing a number of relative $B_1$-maps and storing the relative $B_1$-maps for subsequent, in particular repeated use. The $B_1$-maps are used in a method for establishing an actuation sequence including: establishing a quantitative $B_1$-map. establishing normalized $B_1$-maps on the basis of the relative $B_1$-maps and the quantitative $B_1$-map, and establishing an actuation sequence or acquiring magnetic resonance measurement data using the normalized $B_1$-maps. Furthermore, the embodiments relate to an actuation sequence establishment system and a magnetic resonance imaging system including such an actuation sequence establishment system.

20 Claims, 4 Drawing Sheets (51) Int. Cl.
*G01R 33/24* (2006.01)
*A61B 5/055* (2006.01)
*G01R 33/561* (2006.01)
*G01R 33/565* (2006.01)

(56) References Cited

U.S. PATENT DOCUMENTS

| | | | | |
|---|---|---|---|---|
| 2011/0163748 A1* | 7/2011 | Fleysher | ........ | G01R 33/56563 |
| | | | | 324/307 |
| 2011/0241680 A1* | 10/2011 | Mossnang | ........ | G01R 33/5612 |
| | | | | 324/309 |
| 2012/0179023 A1* | 7/2012 | Fuderer | ............ | G01R 33/5612 |
| | | | | 600/410 |
| 2012/0262170 A1* | 10/2012 | Gumbrecht | ........ | G01R 33/5612 |
| | | | | 324/309 |
| 2013/0229176 A1* | 9/2013 | Fautz | .................. | G01R 33/246 |
| | | | | 324/307 |
| 2013/0253876 A1* | 9/2013 | Pfeuffer | ................ | G01R 33/38 |
| | | | | 702/123 |
| 2014/0292333 A1* | 10/2014 | Beck | .................. | G01R 33/543 |
| | | | | 324/309 |
| 2015/0015258 A1* | 1/2015 | Fautz | .................. | G01R 33/246 |
| | | | | 324/309 |
| 2016/0091587 A1* | 3/2016 | Benner | .............. | G01R 33/543 |
| | | | | 324/322 |

* cited by examiner

FIG 1

ESTABLISHING $B_1$-MAPS

CROSS-REFERENCE TO RELATED APPLICATIONS

This application claims the benefit of DE 10 2013 218 224.4, filed on Sep. 11, 2013, which is hereby incorporated by reference in its entirety.

TECHNICAL FIELD

The embodiments relate to methods for establishing $B_1$-maps, methods for establishing a magnetic resonance system actuation sequence using such $B_1$-maps, a $B_1$-map establishment system, an actuation sequence establishment system including such a $B_1$-map establishment system, and a magnetic resonance imaging system including such an actuation sequence establishment system.

BACKGROUND

In a magnetic resonance imaging system (abbreviated to "magnetic resonance system"), the body to be examined may be exposed to a relatively high main magnetic field (the so-called "$B_0$ field"), for example, of 1.5, 3, 7 Tesla or more, with the aid of a main magnetic field system. Radiofrequency excitation signals (e.g., RF signals) are, via a radiofrequency transmission system, emitted by suitable antenna apparatuses with one or more transmission antenna elements. This is intended to lead to the nuclear spins of specific atoms or molecules, which are excited in a resonant fashion by this radiofrequency field, being tilted by a defined flip angle in relation to the magnetic field lines of the main magnetic field. The resulting flip angle distribution is also referred to as nuclear magnetization or abbreviated to "magnetization" in the following text. When the excited nuclear spins relax, radiofrequency signals, (so-called magnetic resonance signals), are emitted. The radiofrequency signals are received by suitable reception antennas and processed further. Timed to coincide with this, a gradient magnetic field is additionally superposed on the main magnetic field for selective excitation or for spatial encoding of the magnetic resonance signals with the aid of a gradient system. The desired image data may be reconstructed from the raw data acquired. In conventional systems, the emission of the radiofrequency signals (e.g., the so-called $B_1$-field) for nuclear spin magnetization may be brought about by a so-called "whole body coil" (e.g., "body coil") that is securely arranged around the measurement space (patient tunnel). The magnetic resonance signals may be received with the aid of so-called local coils that are positioned more closely to the body of the patient. In principle, magnetic resonance signals may also be received by the whole body coil and/or the RF signals may be transmitted by the local coils.

For a specific measurement, a magnetic resonance system actuation sequence (also abbreviated to "actuation sequence") with a radiofrequency pulse train to be emitted (e.g., RF pulse train, in particular, a sequence of excitation signals in time) and a gradient pulse train may be switched in a manner coordinated therewith for controlling the gradient system (e.g., with appropriate gradient pulses in the slice selection direction, in the phase encoding direction and in the readout direction or frequency encoding direction, often in the z-direction, y-direction, and x-direction) and further control prescriptions is generated in advance. To this end, a multiplicity of parameters and control prescriptions for the actuation sequence are defined in a so-called measurement protocol or control protocol. By way of example, this measurement protocol may be recalled from a memory for a specific measurement and may be modified by the user in situ. During the measurement, the magnetic resonance system may be controlled fully automatically on the basis of this actuation sequence, where the control apparatus of the magnetic resonance system reads and works through commands from the measurement protocol.

In order to generate the actuation sequences, of an RF pulse train in particular, a target magnetization, e.g., a desired spatial flip angle distribution, may be prescribed (e.g., by the measurement protocol and/or by the user). An appropriate RF pulse train is calculated by a suitable RF pulse optimization program, which may operate using a numerical optimization method using a target function to be optimized or minimized such that this target magnetization is obtained.

To this end, current "field distribution maps," (e.g., field distribution maps taking into account the current examination object and the current examination arrangement), may be required. These field distribution maps include, in particular, the "$B_1$-maps," which in each case may specify the spatial field distribution for a specific transmission antenna element or for a combination of transmission antenna elements. The field distribution may be specified in uT/V as a function of the location $\vec{r}$, e.g., the field strength per RF amplitude. In particular, the spatial sensitivity describes the spatial dependence of the flip angles generated by the transmission antenna element or the combination in the region of the measurement space (e.g., in particular over the so-called "field of view" of the magnetic resonance imaging system). Therefore, the $B_1$-maps directly or indirectly describe the circular component of the $B_1$-field (e.g., the so-called $B_1^+$-field) that rotates in the circumferential direction of the nuclear magnetization. Another type of field distribution maps is the so-called "$B_0$-maps," in which the spatial distribution of the main magnetic field (e.g., $B_0$-field) is reproduced, in particular, also occurring inhomogeneities.

The field distribution maps are taken into account in the optimization method in order to find the ideal actuation sequence for the measurement to be carried out for the current examination object in the current examination surroundings.

The information for the $B_1$-maps is often used in the target function to avoid inhomogeneities or geometric distortions of the $B_1$-field or of the $B_1^+$-field, for example, due to radiofrequency shimming (e.g., $B_1^+$-shimming), in a spatially selective excitation by the transmission antenna elements. Falsifications, caused thereby, of the raw data for the magnetic resonance images may often be eliminated or at least strongly reduced. Knowledge of the spatial sensitivity of the affected transmission coils or transmission antenna elements with respect to the current examination object may be an important demand for being able to calculate ideal pTX-RF pulse sequences. This knowledge may be particularly useful in the case of so-called parallel transmission methods (e.g., pTX methods), in which radiofrequency pulses (which in combination form the radiofrequency pulse train) are emitted by a plurality of independently actuatable transmission channels or transmission antenna elements, and which then superpose in the measurement space in order to obtain an individually definable radiofrequency field.

Since the sensitivity of each transmission antenna element or transmission channel is required for each slice or for each image volume, the acquisition of the field distribution maps, in particular of the $B_1$-maps that may be used for the aforementioned optimization method, is relatively time consuming and substantially increases the overall examination duration within clinical routine.

SUMMARY AND DESCRIPTION

It is therefore an object of the present embodiments to specify an option for establishing a magnetic resonance system actuation sequence for acquiring magnetic resonance signals of an examination object, which takes field distribution maps into account, in which the overall time for establishing the actuation sequence and, in particular, $B_1$-maps may be significantly reduced.

The embodiments include methods for establishing $B_1$-maps, in particular, for an image volume to be acquired or a slice to be acquired of an examination object. The maps may be used for establishing an actuation sequence for a magnetic resonance imaging system with a number, (e.g., a plurality), of transmission channels. Here, the transmission channels serve for generating a radiofrequency field or RF pulse train as set forth at the outset. The radiofrequency field or pulse train is used for magnetic resonance excitation of an examination object in the image volume in the magnetic resonance imaging system, for example, for generating the so-called $B_1$-field or $B_1^+$-field, with the aid of transmission antenna elements of a magnetic resonance imaging system. Here, the transmission channels may be operated independently, e.g., they may in each case be actuated individually. Here, a respective transmission antenna element may be assigned to each transmission channel such that the transmission antenna element may be operated independently as set forth at the outset. It is also feasible for a plurality of transmission antenna elements, (e.g., a group of transmission antenna elements), to be assigned to a transmission channel, which transmission antenna elements are then to be operated independently as a group.

The method for establishing $B_1$-maps includes the following acts.

In act 1a, a first radiofrequency field (e.g., a radiofrequency pulse train) is emitted using a transmission channel of the magnetic resonance imaging system. It is feasible for only one transmission channel of the magnetic resonance imaging system to be activated during the emission of the first radiofrequency field. However, particular advantages, explained in conjunction with the developments, may be obtained if further available transmission channels of the magnetic resonance imaging system are activated simultaneously, to be precise in such a way that here, at least one transmission channel of the magnetic resonance imaging system may remain unused (inactive).

In act 1b, first radiofrequency field measurement values for the emitted radiofrequency field are acquired. Here, a "radiofrequency field measurement value" is a measurement value, (e.g., measured directly), from which information about the radiofrequency field, (so-called "radiofrequency field information"), at a specific location (e.g., within the measurement space set forth at the outset or a homogeneity volume of the magnetic resonance imaging system or image volume) may be obtained or derived, or which measurement value constitutes this radiofrequency field information itself. By way of example, the radiofrequency field measurement values may be raw magnetic resonance data.

In act 1c, a relative $B_1$-map on the basis of the first radiofrequency field measurement values is created. In $B_1$-maps, it is possible to distinguish between a plurality of types of field distribution maps that reproduce a field distribution (e.g., the spatial sensitivity) of "radiofrequency field values," respectively in a type-specific form, (e.g., with the aid of type-specific "radiofrequency field information"). In particular, it is possible to distinguish between relative $B_1$-maps and quantitative $B_1$-maps.

In the case of so-called "quantitative $B_1$-maps," the radiofrequency field information is specified in the form of radiofrequency field values, e.g., as numerical value of a field strength. A physical unit (e.g., field strength) is assigned to the radiofrequency field values. By way of example, the radiofrequency field value may be a magnetic field strength. The conventional establishment methods for an actuation sequence may require this form of $B_1$-maps.

In the case of so-called "relative $B_1$-maps," the radiofrequency field information is available in the form of a scaling factor in relation to a reference value. That is to say, the radiofrequency field information of the relative $B_1$-maps may not have units. By way of example, the reference value may be a radiofrequency field value that, for example, may be obtained by a further measurement of radiofrequency field measurement values, in particular carried out in advance. It is also feasible for a measurement value of a factory calibration to serve, at least in a supportive manner, as a reference value.

The radiofrequency field value b1 at a specific location in the measurement space may be established with the aid of a "relative $B_1$-map," as explained in the following. Here, radiofrequency field information for a specific location or section of the measurement space is specified as a numerical value x in the relative $B_1$-map. The following applies:

$$b1 = x \cdot br \quad (1)$$

Here, br is the reference value determined in a preceding measurement and the numerical value x constitutes a scaling factor, e.g., the radiofrequency field information by which the reference value br is multiplied in order to obtain the radiofrequency field value b1. Since the radiofrequency field value is described with the aid of a relative variable, it is only possible with difficulties to use the "relative $B_1$-maps" in a method for establishing an actuation sequence. An advantage of the relative $B_1$-maps is that the relative variable may be obtained by a single additional measurement in relation to the measurement of the reference value, while the "quantitative $B_1$-maps" in each case require at least two measurements per radiofrequency field value, and measuring a "quantitative $B_1$-map" for a transmission channel or for a channel combination may take longer than measuring the "relative $B_1$-map."

What the different types of $B_1$-maps have in common is that a plurality of individual spatial sections of a measurement space in a magnetic resonance imaging system in each case have specific, defined radiofrequency field information assigned to them.

The spatial sections in each case have a predetermined, equal, finite measure of area or volume and together form a spatially continuous region of the measurement space. The measurement space is then described by radiofrequency field information that is available with a specific spatial resolution determined by the measure of area or volume of the spatial sections. Here, the spatial resolution of the $B_1$-maps is given by the number of spatial sections per unit area or unit volume (pixel and voxel, respectively) of the measurement space. The spatial resolution may be directionally dependent, e.g., be different in the z-direction than in the x- or y-direction.

The method for establishing $B_1$-maps furthermore may include the following acts. In act 1d, a further (e.g., in particular second) radiofrequency field may be emitted using a further transmission channel that, in particular, was not activated (e.g., inactive) during the preceding emission of the (e.g., first) radiofrequency field. That is to say the employed transmission channels at least partly differ from the preceding emission. Here, the case that further transmission channels of the magnetic resonance imaging system are activated is likewise not precluded. In act 1e, further or second radiofrequency field measurement values may be acquired for the emitted further radiofrequency field. In act 1f, relative $B_1$-map may be created on the basis of the further radiofrequency field measurement values.

In certain embodiments, the emitting, acquiring, and creating acts (1d through 1f) may be repeated, at least for a number of transmission channels that are used in a subsequent acquisition of raw magnetic resonance data from the examination object in the current examination surroundings and with a specific actuation sequence. The transmission channels used for emitting the radiofrequency field in act 1d, in this case, differ by in each case at least one transmission channel from the preceding emissions.

Further additional measurements taking place are not precluded here. By way of example, if a distinct, relative $B_1$-map is created for each transmission channel of the magnetic resonance imaging system using a single transmission channel, it may be possible to carry out a combination measurement using a plurality of, in particular all, transmission channels. That is to say, $B_1$-maps may also be created using a combination of a plurality of transmission antenna elements, and then specify the spatial $B_1$-field distribution or $B_1^+$-field distribution of the combination of transmission antenna elements.

The number of relative $B_1$-maps established in the method may at least correspond to the number of all transmission channels of the magnetic resonance imaging system. In particular, the relative $B_1$-maps are generated in such a way that, in the manner described above, a radiofrequency field value of a radiofrequency field generated by a transmission channel may be assigned to each respective transmission channel. This may be brought about in various ways, which in each case have different advantages and which are described within the scope of developments.

In a further act 1h of the method, one and/or all generated relative $B_1$-maps (e.g. as a $B_1$-map set) are stored for subsequent use. Here, the generated relative $B_1$-maps may also be stored at any other point during the method. In other words, the generated relative $B_1$-maps (in particular, as a set of $B_1$-maps) are made available for multiple subsequent use, e.g., that these may be retrieved repeatedly. By way of example, the respective relative $B_1$-map may also be stored directly after its creation, e.g., after acts 1c and 1f.

Therefore, the method provides a so-called "$B_1$-map framework", which may be used in various ways. Here, an option for retrieval for multiple accesses to relative $B_1$-maps that may be established quickly is made available. This renders it possible to establish a multiplicity of normalized $B_1$-maps on the basis of a few established quantitative $B_1$-maps, which normalized $B_1$-maps may be used, in particular, in a method for establishing an actuation sequence for a magnetic resonance imaging system. A method and/or a device that provide this option for retrieval is also, as in the following, referred to as a "$B_1$-map framework."

As mentioned previously, the method for establishing $B_1$-maps may, for example, be used in a method for establishing an actuation sequence for a magnetic resonance imaging system. The method for establishing an actuation sequence includes the following acts. In act 2a, a number of relative $B_1$-maps is established, in particular in accordance with acts 1a to 1c of the method for establishing $B_1$-maps, and the relative $B_1$-maps are stored for subsequent use, for example, for multiple retrieval of the stored relative $B_1$-maps from a memory module, (e.g., in accordance with act 1h of the method for establishing $B_1$-maps).

In act 2b, a quantitative $B_1$-map is established. Here, acts 2a and 2b of the method for establishing an actuation sequence may be executed in any order, e.g., at least partly in parallel.

In act 2c, normalized $B_1$-maps are established on the basis of the relative $B_1$-maps and the quantitative B1-map. Here, the so-called "normalized $B_1$-maps" are quantitative $B_1$-maps that are generated, e.g., with the aid of the relative $B_1$-maps and the quantitative $B_1$-map.

As mentioned previously, quantitative $B_1$-maps may be used to establish an actuation sequence for acquiring magnetic resonance measurement data. That is to say, the normalized $B_1$-maps are also available in a form that is suitable for use in most methods for establishing an actuation sequence.

A further act of the method, act 2d, relates to establishing an actuation sequence for acquiring magnetic resonance measurement data using the normalized $B_1$-maps.

Therefore, it is possible to reduce the complicated creation of quantitative $B_1$-maps to a few $B_1$-maps, such as to a single measured $B_1$-map per slice of the examination object to be acquired, in particular for establishing an actuation sequence of a magnetic resonance imaging system. This is achieved by the use of stored relative $B_1$-maps, e.g., by using the "$B_1$-map framework." The relative $B_1$-maps may be generated with significantly less time expenditure than quantitative $B_1$-maps. Moreover, the stored relative $B_1$-maps may be used for a multiplicity of different methods for establishing quantitative $B_1$-maps for different actuation sequences or for different methods of establishment.

Therefore, the embodiments also relate to methods for operating a magnetic resonance imaging system, in which, initially, a magnetic resonance actuation sequence is established using a method and, then, the magnetic resonance imaging system is subsequently operated using this magnetic resonance actuation sequence.

To this end, use may be made of a $B_1$-map establishment system, which includes an input interface for acquiring radiofrequency field measurement values. Moreover, the $B_1$-map establishment system likewise includes a $B_1$-map establishment module for establishing a quantitative $B_1$-map on the basis of the radiofrequency field measurement values. Furthermore, the $B_1$-map establishment system also includes a memory module for repeated or subsequent recalling of relative $B_1$-maps from the memory module.

The $B_1$-map establishment system moreover contains a $B_1$-map normalization module for establishing a number of normalized $B_1$-maps. Here, the normalized $B_1$-maps are established using relative $B_1$-maps recalled from the memory module and the quantitative $B_1$-map.

In particular, the memory module may be used advantageously if, for example, further normalized $B_1$-maps are to be generated on the basis of the previously generated and stored relative $B_1$-maps. This is because the input interface may continue to acquire second radiofrequency field measurement values and the $B_1$-map establishment module may also be used for establishing a further quantitative $B_1$-map on the basis of the further or second radiofrequency field measurement values. Then, the $B_1$-map normalization module may be embodied to establish a number of normalized second $B_1$-maps using a first set of relative $B_1$-maps recalled from the memory module and the second quantitative $B_1$-map. That is to say, the stored relative $B_1$-maps (e.g., of the first $B_1$-map set) are used repeatedly, where a stored relative $B_1$-map may be used to establish two different normalized (e.g., quantitative) $B_1$-maps.

Here, in particular, the memory module is used in such a way that, in order to establish the further normalized $B_1$-maps, after establishing the normalized $B_1$-maps, (and, in certain embodiments, an associated actuation sequence), there is no renewed determination of the relative (e.g., first) $B_1$-maps used for generating the further normalized $B_1$-maps.

An actuation sequence establishment system is proposed, which includes a $B_1$-map establishment system and a sequence establishment unit for establishing an actuation sequence for acquiring magnetic resonance measurement data using the first normalized $B_1$-maps. As mentioned previously, the actuation sequence establishment system may moreover be embodied to establish a further actuation sequence using the further normalized $B_1$-maps, for example, using the stored relative $B_1$-maps. In this case, the stored relative $B_1$-maps are recalled from the memory module and need not be determined again, and so this results in a huge speed advantage when using the actuation sequence establishment system.

The embodiments also relate to a magnetic resonance imaging system, which includes a $B_1$-map establishment system and/or an actuation sequence establishment system. The magnetic resonance imaging system may include an acquisition apparatus for acquiring raw magnetic resonance data or magnetic resonance signals using the actuation sequence.

Essential parts of the $B_1$-map establishment system or of the actuation sequence establishment system may be realized in the form of software on a suitable programmable computer, for example, of a medical imaging system or of a terminal, with appropriate storage options. By way of example, the interfaces may be interfaces that may select or import data from a data memory—optionally also using a user interface—arranged within the medical imaging system and/or actuation sequence establishment system or connected thereto via a network. Furthermore, the systems may in each case have output interfaces in order to transfer the generated data to other apparatuses for further processing, display, memory, etc. An implementation largely in terms of software, in particular, of the $B_1$-map establishment system and/or of the actuation sequence establishment system, is advantageous in that previously used $B_1$-map establishment systems, actuation sequence establishment systems, medical imaging systems, or the like may also be updated in a simple manner by a software update.

In this respect, the object is also achieved by a computer program product that is, e.g., stored in portable memory and/or provided for transmission over a network, and thus may be loaded directly into one or more memories of the magnetic resonance imaging system, the actuation sequence establishment system and/or the $B_1$-map establishment system. The computer program product includes program code sections to execute all acts of the method if the program is executed in the suitable programmable computer. By way of example, the computer may be part of the magnetic resonance imaging system, the actuation sequence establishment system, and/or the $B_1$-map establishment system. Here, the computer program product may, in particular, be encoded in memory that is non-volatile.

A development of the method for establishing an actuation sequence furthermore includes the following acts. In one act, a further, second quantitative $B_1$-map is established, e.g., for the same image volume or the same section of the measurement space, in particular, of an axial slice of the examination object, for which the first quantitative B1-map was already established in advance. This establishment of the further quantitative B1-map is, in particular, carried out for a further actuation sequence for acquiring raw magnetic resonance data. In particular, the further actuation sequence may be a different type of actuation sequence than the first actuation sequence. In particular, types of actuation sequences may be distinguished from one another by the type of the generated contrast, the type of the trajectory or of the covered volume; that is to say, in the case of actuation sequences, which, for example, are based on a turbo flash method (TFL), in particular with different preparation pulse schemes, and actuation sequences of a different type, which for example are based on the spin echo process (SE). Sequences with so-called "radial trajectories" also represent a different type of actuation sequence than sequences with Cartesian trajectories.

A further act relates to establishing further normalized $B_1$-maps on the basis of the stored, e.g., made available, first relative $B_1$-maps and the further quantitative $B_1$-map.

By way of example, the further quantitative $B_1$-map may have a different measurement error or a different spatial resolution to the first quantitative $B_1$-map, and so this may be used to obtain a different quality of the normalized $B_1$-maps or a different fit of the $B_1$-maps to an actuation sequence. This fit may be optimized, in particular, in view of a specific type of actuation sequence.

By way of example, the relative $B_1$-map may be created with a first spatial resolution and, furthermore, a first measurement error when determining the radiofrequency field measurement value may be assigned to the relative $B_1$-map (or may be derived from the relative $B_1$-map).

Furthermore, the $B_1$-map framework may be designed in such a way that the relative $B_1$-maps are generated with a higher spatial resolution than is necessary for a specific actuation sequence to be generated subsequently. This is advantageous in that the relative $B_1$-maps may be used for a very high number of different actuation sequences or types of actuation sequences. Additionally, quantitative $B_1$-maps, which, in a time-consuming manner, are to be established, may be acquired with a spatial resolution required precisely for the respective measurement, for example, also with a low spatial resolution, which, in particular, may be lower than the resolution of the relative $B_1$-maps.

Hence, it becomes possible, in a time-efficient manner, to establish quantitative $B_1$-maps in the form of normalized $B_1$-maps for a multiplicity of measurements or actuation sequences. The $B_1$-maps may be used for establishing an actuation sequence for the magnetic resonance imaging system, where the acquisition of a single quantitative $B_1$-map per actuation sequence and slice to be measured, as per act 2b of the method for establishing an actuation sequence, may suffice.

Accordingly, a further act may relate to establishing a further, second actuation sequence for acquiring magnetic resonance signals, which may be a different type of actuation sequence than the previously (in particular, directly before in time) established actuation sequence, using the further normalized $B_1$-maps.

That is to say, for example, an actuation sequence for a turbo spin echo magnetic resonance imaging method (TSE) may be established in a first act and an actuation sequence may be established for a spin echo-based magnetic resonance imaging method (SE) on the basis of the further quantitative $B_1$-map. The number of the specific quantitative $B_1$-maps, which are established with much time outlay, is reduced to a minimum in the process by generating further normalized $B_1$-maps such that the overall time for establishing $B_1$-maps that, in particular, may be used for creating the plurality of actuation sequences, which may be different types, may be significantly reduced.

As mentioned above, it is also possible to temporally optimize the generation of relative $B_1$-maps. In a development of the method, the number of generated (e.g., first or further) relative $B_1$-maps corresponds at least to a number of transmission channels for generating a radiofrequency field in a measurement space of the magnetic resonance imaging system.

In particular, the number of transmission channels is prescribed in such a way that these transmission channels are used explicitly for creating magnetic resonance images of the examination object in a measurement to be carried out subsequently. This may be some of all the transmission channels of the magnetic resonance imaging system, but the number of transmission channels may include all transmission channels of the magnetic resonance imaging system.

In particular, in a development of the method, the number of generated relative $B_1$-maps may exactly correspond to the number of transmission channels for generating a radiofrequency field in a measurement space of the magnetic resonance imaging system. In this case, an ideal combination of transmission channels may be established, which combination enables a creation of normalized $B_1$-maps for generating the actuation sequence with few quantitative $B_1$-maps, in particular, with a single quantitative $B_1$-map per image volume and a number of generated relative $B_1$-maps, where the number exactly corresponds to the number of transmission channels for generating a radiofrequency field in a measurement space of the magnetic resonance imaging system.

Here, a combination of transmission channels is understood to provide the group of transmission channels that, in particular, are activated simultaneously for generating a specific radiofrequency field. That is to say, specifying a combination of transmission channels at the same time also supplies the complementary information relating to which transmission channels are not used for generating a specific radiofrequency field. Hence, in order to represent a used combination of transmission channels, each of the aforementioned items of information or a combination of the specification of the used transmission channels and not-used transmission channels may be used.

In this optimized combination, the number of generated normalized $B_1$-maps and/or, for example, also the number of the further normalized $B_1$-maps at least corresponds to the number of transmission channels that are used for generating the specific radiofrequency field. Hence it is possible, for example, to generate an associated normalized $B_1$-map for each transmission channel, and so it is unnecessary to acquire additional quantitative $B_1$-maps for a specific transmission channel.

In particular, this may be achieved by virtue of generating at least one relative $B_1$-map using a combination of a plurality of transmission channels of the magnetic resonance imaging system. In the following text, a combination of a plurality of transmission channels may be understood to provide a "so-called linear combination of transmission channels." This is distinguished in that the specific radiofrequency field may be described as a superposition of the radiofrequency fields from a plurality of transmission channels by a linear functional representation (e.g., linear function of the superposition of the transmission powers or of the radiofrequency fields of the individual transmission channels). This demand is not self-evident, particularly in the case of high main magnet field strengths of 7 Tesla and more. However, a person skilled in the art is well aware of the boundary conditions under which it is possible to represent the radiofrequency field with the aid of the linear superposition of radiofrequency fields that were generated using a plurality of independent transmission channels. In order to provide that the linear superposition condition applies, the flip angle at each location is sufficiently small so that the "low flip angle regime" may be employed.

Here, the expression "using a combination of a plurality of transmission channels" provides, in particular, the emission of a radiofrequency field with each transmission channel included in the combination, where, in particular, a plurality of transmission channels may be operated simultaneously.

In a development of the method, all relative $B_1$-maps of the number of relative $B_1$-maps may be generated using a combination of a plurality of transmission channels of the magnetic resonance imaging system. That is to say that information that reproduces the field distribution as a combination of the transmission field (e.g., radiofrequency field) of a plurality of transmission channels is included in all relative $B_1$-maps. Hence, in particular, a large part of the field of view of the magnetic resonance imaging system or of the measurement space may be described by radiofrequency field information in each one of the generated $B_1$-maps and possible shielding effects (e.g., "$B_1$-shimming") may be identified in the process.

In a development of the method, the first quantitative $B_1$-map and/or the further, second quantitative $B_1$-map are generated using a combination of a plurality of transmission channels of the magnetic resonance imaging system. This is particularly advantageous if at least two transmission channels of a combination of transmission channels used for generating the quantitative $B_1$-map are contained in a combination of transmission channels also used for generating at least one of the relative $B_1$-maps. Here, for example, the combination of transmission channels used for generating the quantitative $B_1$-map may exactly correspond to the combination of transmission channels that is used for generating at least one of the relative $B_1$-maps.

Therefore, it is possible, in particular, to carry out an exact inverse calculation with the aid of a single quantitative $B_1$-map if the linear combination of transmission channels is known and, in the process, to generate a number of normalized $B_1$-maps that exactly correspond to the number of transmission channels that are used for generating a magnetic resonance image.

In order to create the quantitative $B_1$-map, a predetermined quality criterion may, particularly advantageously, be used or predetermined to determine the quantitative $B_1$-map. By way of example, as already explained in respect of creating the relative $B_1$-maps, it is possible that the spatial resolution and/or the measurement error of radiofrequency field values (or of radiofrequency field measurement values) is required less exactly for specific actuation sequences or a specific type of actuation sequences than for a different actuation sequence or a different type. This may be taken into account in the predetermined quality criterion. That is to say, the predetermined quality criterion may, for example, be a spatial resolution of the quantitative $B_1$-map and/or a measurement error such as, in particular, a proportionate, (e.g., percentage), measurement error in the determination of the quantitative $B_1$-map. The relative $B_1$-maps may exceed the predetermined quality criterion used for the quantitative $B_1$-map. That is to say, as already mentioned above, a quality criterion may be predetermined or, for example, established or derived from available relative $B_1$-maps when creating the relative $B_1$-maps. If the relative $B_1$-maps exceed the quality criterion for the quantitative $B_1$-maps, it is possible to generate normalized $B_1$-maps that meet the quality criterion predetermined by the quantitative $B_1$-maps. The quality criterion may be predetermined for both the relative $B_1$-maps and the quantitative $B_1$-maps by, in particular, radiofrequency field measurement values being analyzed and the quality criterion, for example, in the form of a spatial resolution and/or in the form of a measurement error, being derived therefrom.

In order, in particular, to provide that the normalized $B_1$-maps also meet the quality criterion predetermined, in particular, by the quantitative $B_1$-maps, there may be a comparison of a quality criterion for relative $B_1$-maps and a quality criterion for quantitative $B_1$-maps in a development of the method. In particular, this comparison may be a comparison of the spatial resolutions and/or of measurement errors. In the process, it is possible to check whether the spatial resolution of one or all of the relative $B_1$-maps achieves or exceeds the spatial resolution of the quantitative $B_1$-map and/or whether an in particular proportionate percentage measurement error of one or all of the relative $B_1$-maps achieves or exceeds an in particular proportionate percentage measurement error of the quantitative $B_1$-map.

By way of example, if the spatial resolution of the quantitative $B_1$-map is less than or equal to the spatial resolution of the relative $B_1$-maps, normalized $B_1$-maps with the spatial resolution of the quantitative $B_1$-map may be created in any case. That is to say, the created normalized $B_1$-maps satisfy the quality criterion predetermined by the quantitative $B_1$-map in respect of the spatial resolution. By way of example, the quantitative $B_1$-map may likewise be analyzed in respect of the measurement error of the underlying measurement data. Additionally, in an analogous manner, it may be possible to provide that the created normalized $B_1$-maps satisfy the quality criterion predetermined by the quantitative $B_1$-map in respect of the measurement error.

In particular, if it is determined that it is not possible to create normalized $B_1$-maps that satisfy the quality criterion that was predetermined for the quantitative $B_1$-map, it is possible, in a development of the method for establishing an actuation sequence on the basis of the comparison of act 1a, to repeat, (e.g., in particular, the emission of a first radiofrequency field using a transmission channel), the acquisition of radiofrequency field measurement values for the emitted radiofrequency field and the creation of a relative $B_1$-map on the basis of the first radiofrequency field measurement values. This may be conducted in order then to store this in accordance with act 1h of the method and make it available for later use, (e.g., for multiple recalling from the memory module). Furthermore, it is possible to establish the normalized $B_1$-maps in accordance with act 2c or 2g and use these normalized $B_1$-maps to establish an actuation sequence in accordance with act 2d or 2h.

That is to say, a repetition of the acquisition of the relative $B_1$-maps (in accordance with act 1a)) may be carried out if, in particular, the spatial resolution of one of the relative $B_1$-maps drops below the spatial resolution of the quantitative $B_1$-map and/or if a proportionate percentage measurement error of one of the relative $B_1$-maps exceeds a proportionate percentage measurement error of the quantitative $B_1$-map. In order to repeat the acquisition of the relative $B_1$-maps, it is possible to use an actuation sequence that takes into account the predetermined quality criterion for the quantitative $B_1$-map such that the generated relative $B_1$-maps meet the quality criterion that was predetermined (e.g., for the quantitative and/or relative $B_1$-map). In the process, a fast gradient echo-based method or a fast gradient echo-based actuation sequence may be used.

The $B_1$-map establishment system, which serves to establish normalized $B_1$-maps, may include a $B_1$-map generation module embodied for generating relative $B_1$-maps on the basis of radiofrequency field measurement values. In particular, the $B_1$-map generation module is connected to the memory module for storing the generated relative $B_1$-maps such that these may be recalled from the memory module for subsequent use.

The $B_1$-map establishment system may also include a quality criterion interface for predetermining the aforementioned quality criterion for quantitative $B_1$-maps such that, for example, normalized $B_1$-maps may be generated for the actuation sequence, which normalized $B_1$-maps satisfy a different quality criterion than the quantitative $B_1$-map and/or the relative $B_1$-map.

This quality criterion may then be used in a $B_1$-map analysis apparatus that is included in the $B_1$-map establishment system. The $B_1$-map analysis apparatus is configured to compare the quality of relative $B_1$-maps and quantitative $B_1$-maps on the basis of the quality criterion, and may be configured to trigger the generation of further relative $B_1$-maps on the basis of the comparison, e.g., in particular the acquisition of radiofrequency field measurement values. To this end, the $B_1$-map analysis apparatus may include a trigger interface for emitting a trigger signal that triggers the acquisition of radiofrequency measurement values for determining quantitative and/or relative $B_1$-maps. As mentioned previously, it is therefore possible within the $B_1$-map framework to provide that the generated normalized $B_1$-maps satisfy a predefined quality criterion and may be used for establishing an actuation sequence.

The scope of the present invention is defined solely by the appended claims and is not affected to any degree by the statements within this summary. The present embodiments may obviate one or more of the drawbacks or limitations in the related art.

DETAILED DESCRIPTION

Figure 1:
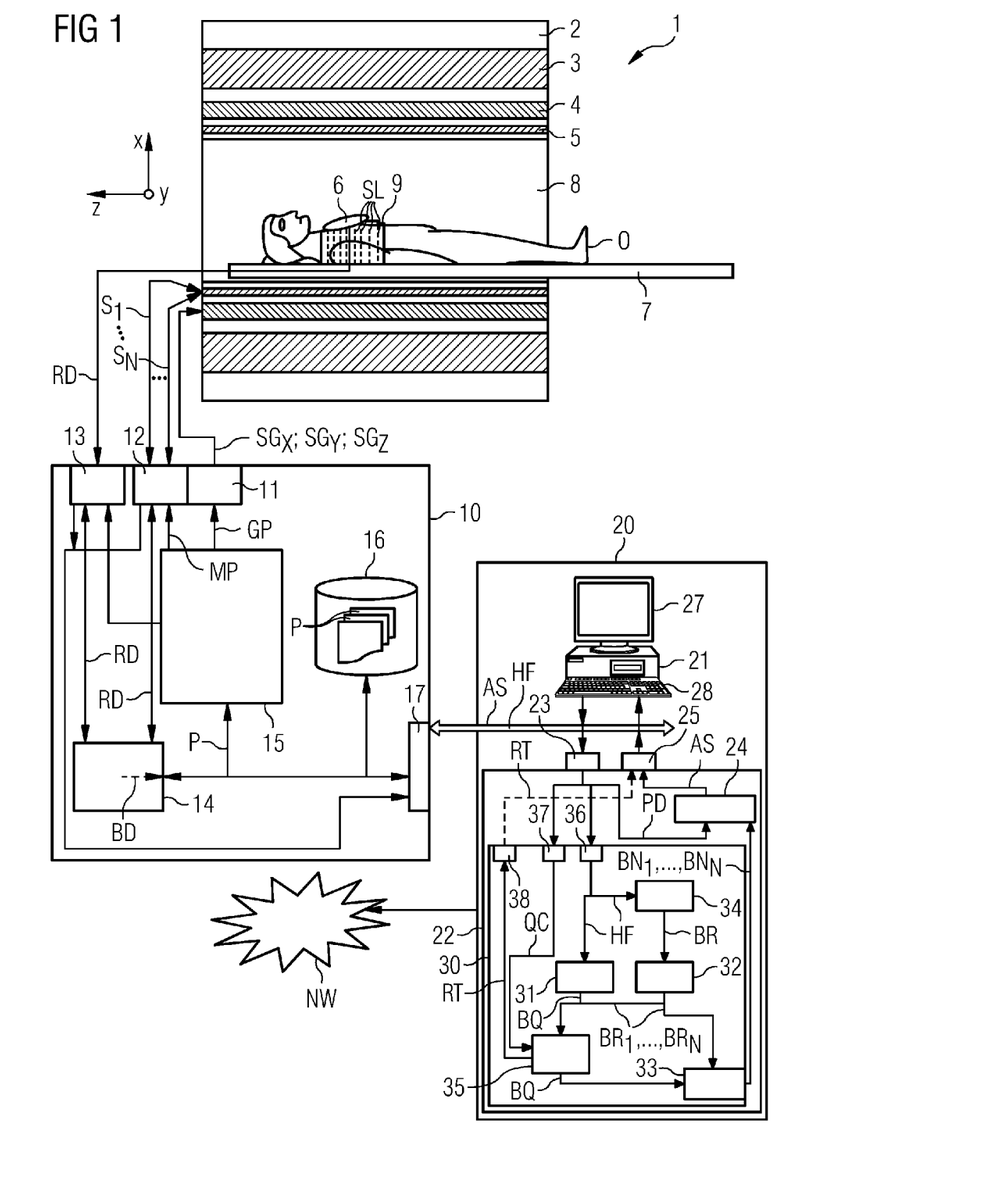
FIG. 1 depicts an exemplary embodiment of a magnetic resonance imaging system.

FIG. 1 depicts an embodiment of a magnetic resonance installation 1 in a schematic manner. The magnetic resonance installation includes the actual magnetic resonance scanner 2 with a measurement space 8 or patient tunnel situated therein. A couch 7 may be driven into this patient tunnel 8 such that an examination object O (e.g., patient/subject) lying thereon may, within the scope of an examination, be displaced to a specific position within the magnetic resonance scanner 2 relative to the radiofrequency system and magnet system arranged therein, and may also be displaced between various positions during a measurement.

Components of the magnetic resonance scanner 2 include a main field magnet 3, a gradient system 4 with gradient coils for setting arbitrary magnetic field gradients in the x-, y- and z-direction, and a whole-body radiofrequency coil 5. Magnetic resonance signals induced in the examination object O may be received by the whole-body coil 5, by which the radiofrequency signals for inducing the magnetic resonance signals may also be emitted. However, these signals may be received by local coils 6 that are, e.g., placed onto or below the examination object O. In principle, a person skilled in the art is well acquainted with all these components and hence these are only depicted very schematically in FIG. 1.

The whole-body radiofrequency coil 5 may, e.g., in the form of a so-called birdcage antenna, have a number N of individual antenna rods, which may, as individual transmission channels $S_1, \ldots, S_N$, be actuated separately by a control apparatus 10, e.g., the magnetic resonance imaging system 1 is a pTX-capable system. However, reference is explicitly made to the fact that the method may also be applied to conventional magnetic resonance imaging devices with only one transmission channel.

The control apparatus 10 may be a control computer that may also include a multiplicity of individual computers, which, optionally, are also spatially separated and interconnected by suitable bus systems and cables or the like. By a terminal interface 17, this control apparatus 10 is connected to a terminal 20, by which an operator may actuate the whole installation 1. In the present case, this terminal 20 includes a computer 21 with a keyboard 28, one or more monitors 27, and further input devices such as, e.g., a mouse or the like, and so a graphical user interface is available to the operator.

The control apparatus 10 includes a gradient control unit 11, which in turn may include a plurality of partial components. Control signals $SG_x$, $SG_y$, $SG_z$ are applied to the individual gradient coils by this gradient control unit 11. The control signals are gradient pulses that, during a measurement, are emitted at precisely envisaged positions in time and with a precisely predetermined time profile.

The control apparatus 10 moreover includes a radiofrequency transmission/reception unit 12. This RF transmission/reception unit 12 likewise includes a plurality of partial components so as to emit radiofrequency pulses, in each case separately and in parallel, to the individual transmission channels $S_1, \ldots, S_N$, e.g., to the individual actuatable antenna rods of the body coil 5. It is also possible to receive magnetic resonance signals by the transmission/reception unit 12. However, this is brought about with the aid of the local coils 6 in this exemplary embodiment. The raw data RD received by these local coils 6 are read out by an RF reception unit 13 and processed. The magnetic resonance signals received hereby, or by the whole-body coil 5, by the RF transmission/reception unit 12 are transmitted as raw data RD to a reconstruction unit 14, which reconstructs the image data BD therefrom and stores these in a memory 16 and/or transmits these to the terminal 20 via the interface 17 such that these may be observed by the operator. The image data BD may also be stored and/or displayed and evaluated at different locations via a network NW. To the extent that the local coils 6 include a suitable switching unit, the local coils may also be connected to an RF transmission/reception unit 12 so as to use the local coils for transmission as well, in particular, during pTX-operation.

The gradient controller 11, the RF transmission/reception unit 12, and the reception unit 13 for the local coils 6 are actuated in each case in a coordinated manner by a measurement control unit 15. By appropriate commands, the latter provides that a desired gradient pulse train GP is emitted by suitable gradient control signals $SG_x$, $SG_y$, $SG_z$ and, in parallel, actuates the RF transmission/reception unit 12 in such a way that a multi-channel pulse train MP is emitted, e.g., that the appropriate radiofrequency pulses are transmitted to the individual transmission rods of the whole-body coil 5 on the individual transmission channels $S_1, \ldots, S_N$. It is moreover necessary to provide that, at the appropriate time, the magnetic resonance signals are read out at the local coils 6 by the RF reception unit 13 or that possible signals at the whole-body coil 5 are read out by the RF transmission/reception unit and processed further. The measurement control unit 15 provides the appropriate signals, in particular, the multi-channel pulse train MP, for the radiofrequency transmission/reception unit 12 and the gradient pulse train GP for the gradient control unit 11, in accordance with a predetermined control protocol P. The control data that is set during a measurement is stored in this control protocol P.

A multiplicity of control protocols P for various measurements may be stored in a memory 16. The protocols may be selected by the user via the terminal 20 and, if need be, be varied in order then to have available an appropriate control protocol P for the currently desired measurement, by which control protocol the measurement control unit 15 may operate. Incidentally, the operator may also recall control protocols via a network NW, for example, from a manufacturer of the magnetic resonance system, and then optionally modify and use these.

However, the basic procedure of such a magnetic resonance measurement and the aforementioned components for actuation are known to a person skilled in the art, and so these are not discussed in any more detail here. Incidentally, such a magnetic resonance scanner 2 and the associated control apparatus may include a multiplicity of further components, which are likewise not explained in detail here. However, it is noted here that the magnetic resonance scanner 2 may also have a different design, for example, with a laterally open patient space, and that, in principle, the radiofrequency whole-body coil need not be designed as a birdcage antenna.

In this case, FIG. 1 moreover schematically depicts a control sequence establishment unit 22 that serves to establish a magnetic resonance system actuation sequence AS. This magnetic resonance system actuation sequence AS includes a pulse sequence, for a specific measurement, with a gradient pulse train GP for passing along a specific trajectory in k-space, and, coordinated therewith, a radiofrequency pulse train, in this case a multi-channel pulse train MP, for actuating the individual transmission channels $S_1, \ldots, S_N$. In the present case, the magnetic resonance system actuation sequence AS is created on the basis of parameters PD prescribed in the measurement protocol P.

Here, the control sequence establishment apparatus 22 is depicted as part of the terminal 20 and may be realized on the computer 21 of this terminal 20 in the form of software components. However, in principle, the control sequence establishment apparatus 22 may also be realized as part of the control apparatus 10 itself, or on a separate computer system. The complete actuation sequences AS are transmitted to the magnetic resonance system 1 via a network NW, optionally also within the scope of a complete control protocol P. In certain embodiments, the control sequence establishment apparatus 22 may also establish a current new control sequence on the basis of current initial conditions during a measurement session, that is to say, within the scope of an examination of a patient.

The current $B_1$-maps that are provided for the excitation in the calculation of the ideal RF pulse trains are generated prior to the start of the actual measurement for a plurality of slices SL in a field of view 9 (FoV) within the examination object O, of which magnetic resonance recordings are also intended to be generated. Overall, a plurality of $B_1$-maps, (e.g., at least as many as correspond to the number of used transmission channels N), are required for each slice SL in the method for establishing an actuation sequence AS. By way of example, if, overall, $B_1$-maps are required for 40 slices in a system with 10 used transmission channels, it is therefore provided to establish at least 400 $B_1$-maps. This requires much time and may therefore be carried out as efficiently as possible.

In this case, the control sequence establishment apparatus 22 includes an input interface 23. The control sequence establishment apparatus 22 receives parameters PD for establishing an actuation sequence AS via this input interface 23. The parameters PD include, inter alia, a target magnetization that prescribes the intended flip angle distribution during the desired measurement, a k-space trajectory or a k-space trajectory type and, optionally, further input parameters that, in part, are explained in more detail below in conjunction with FIG. 4. The control sequence establishment apparatus 22 may also import radiofrequency field measurement values HF and/or relative $B_1$-maps $BR_1, \ldots, BR_N$ via this input interface 23.

The control sequence establishment apparatus 22 furthermore includes an RF pulse establishment unit 24 that, in particular, operates as a so-called "optimization unit." The latter establishes a radiofrequency pulse train MP on the basis of the aforementioned input data using a suitable optimization method.

Moreover, the control sequence establishment apparatus 22, in this case, also includes a $B_1$-map establishment system 30. The $B_1$-map establishment system 30 includes an input interface 36, by which radiofrequency field measurement values HF may be imported.

Moreover, the $B_1$-map establishment system 30 includes a $B_1$-map establishment module 31, a $B_1$-map generation module 34, a memory module 32, a $B_1$-map normalization module 33, and a $B_1$-map analysis module 35.

With the aid of the $B_1$-map normalization module 33, a number of normalized $B_1$-maps $BN_1, \ldots, BN_N$ are established on the basis of the radiofrequency field measurement values HF. By an output interface arrangement, these normalized $B_1$-maps $BN_1, \ldots, BN_N$ may be transmitted as input data to the RF pulse establishment unit 24 (e.g., the optimization unit) such that the latter may then work with the normalized $B_1$-maps $BN_1, \ldots, BN_N$ in order to establish the ideal radiofrequency pulse train MP.

Here, the normalized $B_1$-maps $BN_1, \ldots, BN_N$ are created using a "B1-map framework," which provides the option of storing a number of relative $B_1$-maps $BR_1, \ldots, BR_N$ in, and recalling these from, the memory module 32 and transmitting these to the $B_1$-map normalization module 32. In particular, the stored relative $B_1$-maps $BR_1, \ldots, BR_N$ were established in advance for the current examination surroundings and the current examination object, in particular for each slice SL; the details in respect of the initial establishment of relative $B_1$-maps $BR_1, \ldots, BR_N$ (e.g., of a first relative $B_1$-map set) are explained in more detail below.

With the aid of a first quantitative B1-map BQ, which is established by the $B_1$-map establishment module 31 on the basis of the radiofrequency field measurement values HF, the $B_1$-map normalization module 33 generates first normalized $B_1$-maps $BN_1, \ldots, BN_N$ using the relative $B_1$-maps $BR_1, \ldots, BR_N$ recalled from the memory module 32. The number of recalled, first relative $B_1$-maps $BR_1, \ldots, BR_N$ corresponds to the number of transmission channels N of the magnetic resonance imaging system 1 and a specific image volume is created for a specific slice SL of the examination object. An option for establishing normalized $B_1$-maps $BN_1, \ldots, BN_N$ on the basis of relative $B_1$-maps $BR_1, \ldots, BR_N$ and quantitative $B_1$-maps is, for example, described in Van de Moortele et al., "Calibration Tools for RF Shim at Very High Field with Multiple Element RF Coils from Ultra Fast Local Relative Phase to Absolute Magnitude $B_1$ Mapping," Proc. Int'l Soc. Mag. Reson. Med., 2007, Vol. 15, p. 1676, where explanations are provided in respect of, for example, how magnitudes and phase information of the $B_1$-distribution are established from relative and quantitative $B_1$-maps.

Subsequently, the first normalized $B_1$-maps $BN_1, \ldots, BN_N$ are transmitted via an interface to the RF pulse establishment unit 24 for establishing a radiofrequency pulse train MP for a first actuation sequence AS. By way of example, the first actuation sequence is a turbo spin echo-based (TSE) or a turbo flash-based (TFL) sequence and may therefore be considered as belonging to a first type of actuation sequence AS.

After establishing the first actuation sequence AS, this may be output in turn by the control sequence establishment apparatus 22 via an output interface arrangement 25.

In the control protocol P, it is also possible to store whether the actuation sequence AS is intended to be updated during the scope of a measurement session such that a new actuation sequence AS is automatically established in a manner or requested from, e.g., the terminal 20 or a different computer by the control apparatus 10 at the suitable times.

Second normalized $B_1$-maps $BN_1, \ldots, BN_N$ may be provided in order, for example, to generate a second actuation sequence AS, which, in particular, belongs to a second type of actuation sequence AS. In this case, the second type of actuation sequence may be a sequence based on spin echo (SE) or turbo flash (TFL). To this end, second normalized $B_1$-maps $BN_1, \ldots, BN_N$, which, e.g., have a deviating spatial resolution and/or a deviating measurement accuracy, e.g., a greater or smaller measurement error, from the first normalized $B_1$-maps $BN_1, \ldots, BN_N$, are provided for the same image volume or for the same slice SL. That is to say, the second normalized $B_1$-maps $BN_1, \ldots, BN_N$ may have different quality than the first normalized $B_1$-maps $BN_1, \ldots, BN_N$; e.g., they satisfy a different quality criterion QC than the first normalized $B_1$-maps $BN_1, \ldots, BN_N$.

With the aid of the "$B_1$-map framework," it is possible to provide that the normalized $B_1$-maps $BN_1, \ldots, BN_N$ in each case satisfy a quality criterion QC predetermined for an actuation sequence AS.

The $B_1$-map establishment module 31 is embodied to establish quantitative $B_1$-maps BQ in accordance with a predetermined quality criterion QC on the basis of the radiofrequency field measurement values HF.

To this end, the radiofrequency field measurement values HF transferred to the $B_1$-map establishment module 31 are transmitted in parallel to a quality criterion interface 37 that is embodied to establish a quality criterion QC for normalized $B_1$-maps $BN_1, \ldots, BN_N$, e.g., the desired quality thereof thus determined in advance, on the basis of the radiofrequency field measurement values HF. As mentioned previously, the quality criterion QC may be a desired spatial resolution and/or a desired maximum measurement error.

It is also feasible for a quality criterion QC to be transmitted directly to the quality criterion interface 37, which quality criterion may, for example, be created or predetermined by user requirements, in particular, with the aid of the terminal 20. In this case, it is also possible to dispense with establishing a quality criterion QC on the basis of the radiofrequency field measurement values HF and the predetermined quality criterion QC may deviate from the quality of the radiofrequency field measurement values HF.

The quality criterion interface 37 may be optionally connected to the $B_1$-map establishment module 31 or integrated into the $B_1$-map establishment module 31.

By way of example, a desired spatial resolution may be less than the spatial resolution of the radiofrequency field measurement values HF or a permitted maximum measurement error may be greater than a maximum measurement error of the radiofrequency field measurement value HF.

Then, the $B_1$-map establishment module 31 creates a second quantitative $B_1$-map BQ for establishing the second normalized $B_1$-maps $BN_1, \ldots, BN_N$. The second normalized $B_1$-maps are transferred to the $B_1$-map analysis module 35 and, to the $B_1$-map normalization module 33. On the basis of first relative $B_1$-maps $BR_1, \ldots, BR_N$ in turn recalled from the memory module 32, the $B_1$-map normalization module establishes second normalized $B_1$-maps $BN_1, \ldots, BN_N$ that are transferred to the $B_1$-map generation module 24 for generating a second actuation sequence, for example, a different flip angle distribution.

Before this, the $B_1$-map analysis module 35 likewise recalls the first relative $B_1$-maps $BR_1, \ldots, BR_N$ from the memory module 32 in order to establish therefrom a quality criterion QC that the relative $B_1$-maps $BR_1, \ldots, BR_N$ satisfy. Furthermore, the $B_1$-map analysis module 35 compares the established quality criterion with the desired quality criterion QC, which is transferred to the $B_1$-map analysis module 35 before the quality criterion interface 37.

It is also feasible that a quality criterion QC, which the relative $B_1$-maps $BR_1, \ldots, BR_N$ stored in the memory module 32 satisfy, is transmitted from the memory module to the $B_1$-map analysis module 35. In this case, it is possible to dispense with establishing a quality criterion QC for the relative $B_1$-maps $BR_1, \ldots, BR_N$ by the $B_1$-map analysis module 35.

If the comparison yields that the relative $B_1$-maps $BR_1, \ldots, BR_N$ satisfy the desired quality criterion QC, the relative $B_1$-maps $BR_1, \ldots, BR_N$ and the quantitative $B_1$-map BQ may be used for establishing the normalized $B_1$-maps $BN_1, \ldots, BN_N$ in such a way that the latter meet the desired quality criterion QC. Thus, the $B_1$-map normalization module 33 is embodied in such a way that it takes into account the desired quality criterion QC.

By contrast, if the comparison yields that the relative $B_1$-maps $BR_1, \ldots, BR_N$ and/or the quantitative $B_1$-map do not satisfy the desired quality criterion QC, this provides that no normalized $B_1$-maps $BN_1, \ldots, BN_N$ that satisfy the desired quality criterion QC may be established on the basis of the relative $B_1$-maps $BR_1, \ldots, BR_N$ and/or of the quantitative $B_1$-map respectively available in the memory module 32.

In this case, appropriate quantitative $B_1$-maps BQ and/or appropriate relative $B_1$-maps $BR_1, \ldots, BR_N$ are created. If no appropriate relative $B_1$-maps $BR_1, \ldots, BR_N$ for the actuation sequence AS or the predetermined magnetization have yet been stored in the memory module 32, (as this may be the case, e.g., before recalling the relative $B_1$-maps $BR_1, \ldots, BR_N$ from the memory module 32 for the first time), the $B_1$-map analysis module 35 transmits a trigger signal RT for triggering a measurement of radiofrequency field measurement values HF to a trigger interface 38. By way of example, the latter may be connected to an output interface 25 and the trigger signal RT may be configured in such a way that an appropriate actuation sequence AS for generating radiofrequency field measurement values HF that satisfy the desired quality criterion QC is selected from the memory apparatus 16. By way of example, actuation sequences AS suitable for this may be stored in the memory apparatus 16 within the scope of the factory configuration of the magnetic resonance imaging system. For the purposes of a first time generation of the relative $B_1$-maps $BR_1, \ldots, BR_N$, a standard resolution and/or a standard measurement error may be predetermined as quality criterion QC, which is set on the basis of a series or a row of actuation sequences AS to be established.

The radiofrequency field measurement values HF generated on the basis of an appropriate (e.g., factory) actuation sequence AS are, with the aid of the input interface 36, transmitted to the $B_1$-map generation module 34 that establishes at least one relative $B_1$-map BR on the basis of the radiofrequency field measurement values HF. Establishing appropriate relative $B_1$-maps BR may be continued until the number of different relative $B_1$-maps $BR_1, \ldots, BR_N$ required for an examination to be carried out is available. The number of $B_1$-maps may correspond at least to the number of normalized $B_1$-maps $BN_1, \ldots, BN_N$ required for establishing the actuation sequence. The $B_1$-map generation module 34 transfers these to the memory module 32. A detailed explanation of a method for establishing the number of necessary relative $B_1$-maps $BR_1, \ldots, BR_N$ (e.g., for establishing a relative $B_1$-map set) is provided below with reference to FIGS. 2 and 3.

Figure 2:
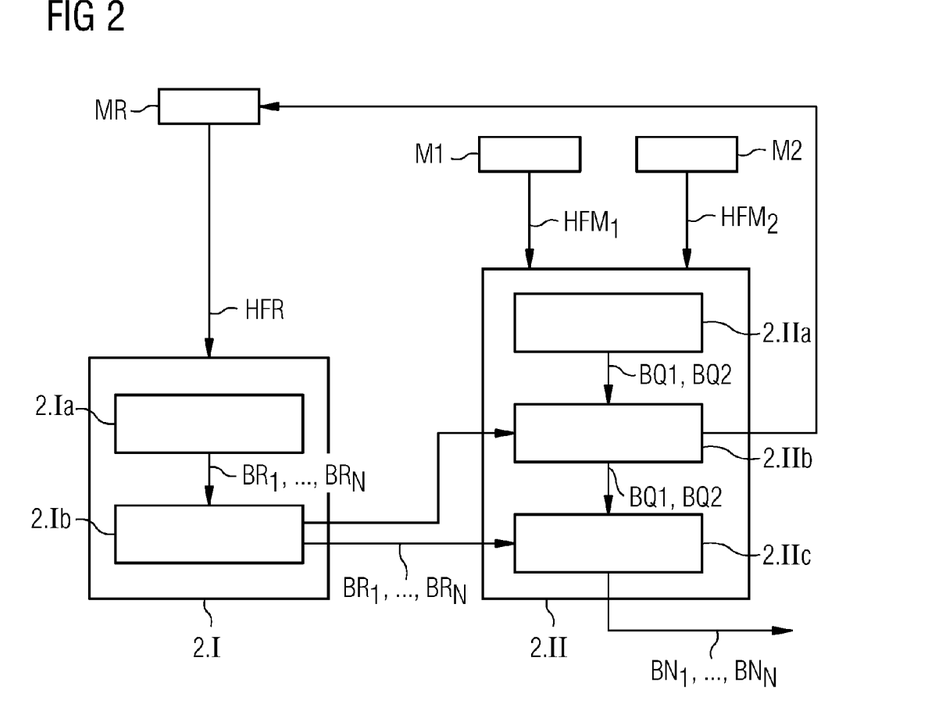
FIG. 2 depicts an exemplary embodiment of a method for establishing field distribution maps.

FIG. 2 depicts a method for establishing normalized $B_1$-maps in a two-stage manner. In a first stage 2.I, radiofrequency field measurement values HFR, which may be used for generating relative $B_1$-maps, are established in a measurement MR. As mentioned previously, appropriate actuation sequences may be part of the factory settings of the magnetic resonance imaging system. In the first stage 2.I, a number of relative $B_1$-maps $BR_1, \ldots, BR_N$ are established on the basis of the radiofrequency field measurement values HFR in a first act 2.Ia. These relative $B_1$-maps $BR_1, \ldots, BR_N$ are subsequently stored in the memory module in a further act 2.Ib. If a first radiofrequency pulse train, which for example serves to establish magnetic resonance measurement data in a specific slice of the examination object, may now be established for a first actuation sequence, further radiofrequency field measurement values HFM1, which are suitable for establishing a quantitative $B_1$-map, are established in a measurement M1.

In a second stage 2.II, a quantitative $B_1$-map BQ1 is established in an initial act 2.IIa on the basis of the radiofrequency field measurement values HFM1.

In an optional subsequent act 2.IIb, the relative $B_1$-maps $BR_1, \ldots, BR_N$ available in the memory module may be examined as to whether they satisfy a quality criterion QC that, for example, is predetermined in respect of the quantitative $B_1$-map BQ1 or may be derived from the quantitative $B_1$-map BQ1 or predetermined by a user.

A number of (e.g., first) normalized $B_1$-maps $BN_1, \ldots, BN_N$ are generated depending on the radiofrequency field measurement values M1 on the basis of the stored relative $B_1$-maps $BR_1, \ldots, BR_N$ and the first quantitative $B_1$-map BQ1 in a further act 2.IIc, may in the case of a positive comparison (e.g., if the relative $B_1$-maps $BR_1, \ldots, BR_N$ satisfy at least one quality criterion QC of the quantitative $B_1$-map—may all predetermined quality criteria). This dependence is predetermined and specified by the first quantitative $B_1$-map BQ1. As mentioned previously, the normalized $B_1$-maps $BN_1, \ldots, BN_N$ may be generated with the aid of the quantitative $B_1$-map BQ1 and the relative $B_1$-maps $BR_1, \ldots, BR_N$, for example, as described in Van de Moortele et al., "Calibration Tools for RF Shim at Very High Field with Multiple Element RF Coils from Ultra Fast Local Relative Phase to Absolute Magnitude $B_1^+$ Mapping," Proc. Int'l Soc. Mag. Reson. Med., 2007, Vol. 15, p. 1676.

Here, the stored relative $B_1$-maps $BR_1, \ldots, BR_N$ may be created in a so-called "low flip angle regime," e.g., with a flip angle or magnetization deflection of less than 10° with respect to the main magnetic field direction. In particular, this provides that they may be measured much faster than quantitative $B_1$-maps BQ1.

Furthermore, the flip angle distribution, which is generated with the aid of a plurality of transmission channels used at the same time, may be functionally described as a linear superposition of the respective transmission field strength or magnetization generated by an individual transmission coil. This may be used, as explained below in relation to FIG. 3, to further accelerate the method for generating the normalized $B_1$-maps $BN_1, \ldots, BN_N$.

In one embodiment, each one of the generated relative $B_1$-maps $BR_1, \ldots, BR_N$ includes two partial maps, where one of the partial maps in each case contains phase information and the other one of the partial maps contains magnitude information. The two partial maps are generated separately from one another, may be within the scope of different measurements.

As already explained in relation to FIG. 1, the first normalized $B_1$-maps $BN_1, \ldots, BN_N$ generated may be used for generating a radiofrequency field pulse train.

By way of example, if a different, further measurement sequence is to be used, for example, if a different magnetization in relation to the first actuation sequence is intended to be generated in the same slice of the examination object, it is possible, in this respect, for further radiofrequency field measurement values HFM2 to be generated within the scope of a further measurement M2. As described in the following text, these are used to generate second normalized $B_1$-maps $BN_1, \ldots, BN_N$.

To this end, a quantitative $B_1$-map BQ2, e.g., a second quantitative $B_1$-map in this case, is generated in turn on the basis of the radiofrequency field measurement values HFM2 in act 2.IIa of the second stage 2.II of the method. In optional act 2.IIb, it is possible to check whether the relative $B_1$-maps $BR_1, \ldots, BR_N$ available in the memory module satisfy the quality criterion of the second quantitative $B_1$-map BQ2. If this is the case, both the relative $B_1$-maps $BR_1, \ldots, BR_N$ and the second quantitative $B_1$-map BQ2 are used to generate a number of second normalized $B_1$-maps $BN_1, \ldots, BN_N$ on the basis of the radiofrequency field measurement values HFM2, as described above.

For the sake of completeness, reference is made here to the fact that the one measurement MR for generating radiofrequency field measurement values HFR may be triggered in the case of a negative comparison in act 2.IIb, (e.g., if the stored relative $B_1$-maps $BR_1, \ldots, BR_N$ do not satisfy the predetermined quality criterion), as described in relation to FIG. 1, which radiofrequency field measurement values may then be used to create suitable relative $B_1$-maps $BR_1, \ldots, BR_N$.

Figure 3:
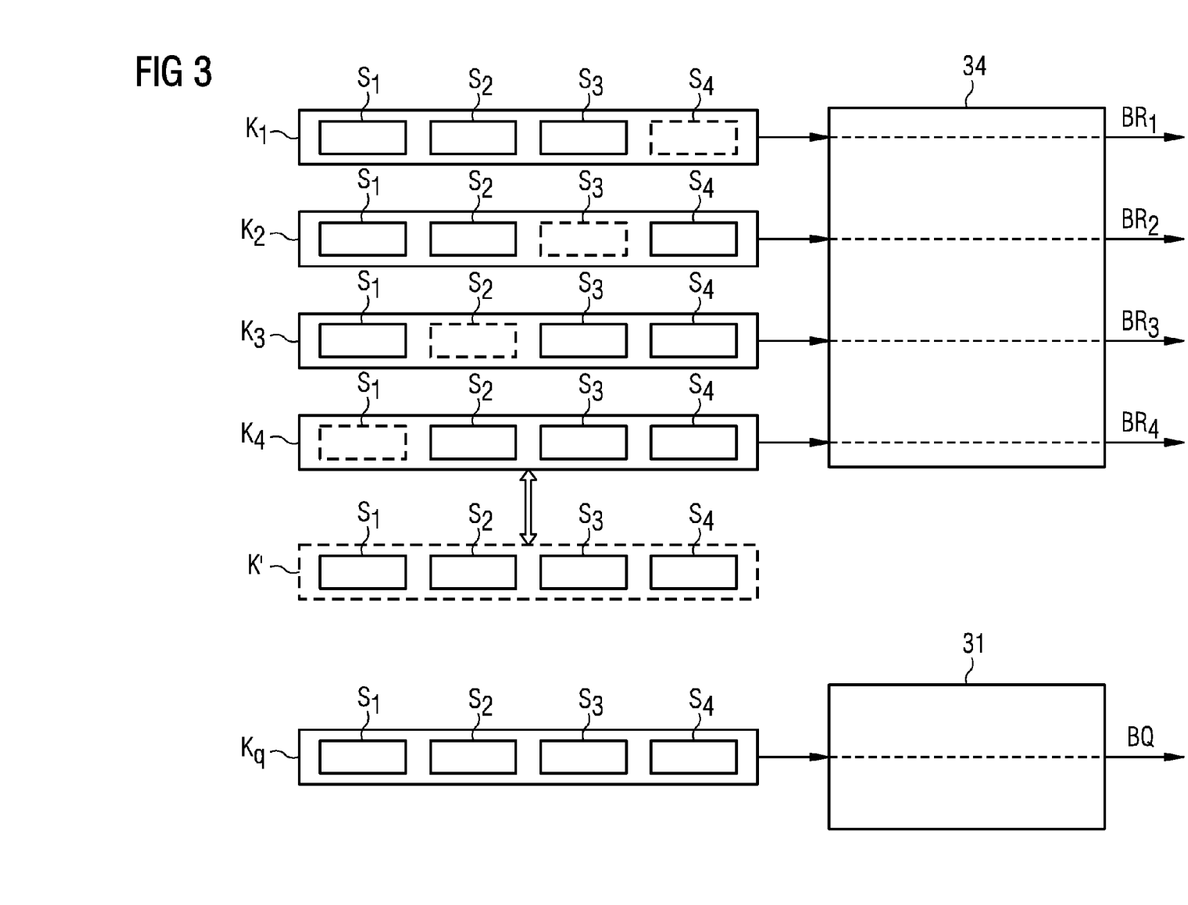
FIG. 3 depicts an exemplary embodiment for using a combination of transmission channels of a magnetic resonance imaging system for establishing field distribution maps.

By way of example, a suitable method for generating relative $B_1$-maps $BR_1, \ldots, BR_N$ is depicted in FIG. 3.

Here, various combinations of transmission channels of the magnetic resonance imaging system may be used for generating radiofrequency field measurement data, for example, in FIG. 2, the radiofrequency field measurement data HFR that are suitable for establishing relative $B_1$-maps. In FIG. 2, the magnetic resonance imaging system includes four transmission channels, e.g., N=4. It is intended that all of these channels are used in combination for generating a target magnetization in a first actuation sequence. Therefore, at least a number of four quantitative $B_1$-maps have to be generated for a slice or image volume within the scope of an optimization method. This is carried out by creating normalized $B_1$-maps. In the present case, at least four relative $B_1$-maps $BR_1, BR_2, BR_3, BR_4$ are made available by the memory module for generating four normalized $B_1$-maps. That is to say, the $B_1$-map generation module 34 establishes at least four relative $B_1$-maps $BR_1, BR_2, BR_3, BR_4$ on the basis of the radiofrequency field measurement data such that the spatial sensitivity of the transmission channels may be calculated from these. To this end, radiofrequency pulses are emitted in the present case, which radiofrequency pulses are generated by using a combination of a plurality of transmission channels $S_1, S_2, S_3, S_4$ of the magnetic resonance imaging system. A first combination $K_1$ includes active transmission channels $S_1, S_2, S_3$. Here, as indicated by the dashed lines, the further transmission channel $S_4$ of the magnetic resonance imaging system 1 is inactive. The further combinations $K_2, K_3$ and $K_4$ are in this case respectively created in such a way that a different one of the transmission channels $S_1, S_2, S_3, S_4$ is inactive while the remaining transmission channels $S_1, S_2, S_3, S_4$ of the magnetic resonance imaging system are actively used in each case. By way of example, in the combination $K_2$, the transmission channels $S_1, S_2$ and $S_4$ are active, while the transmission channel $S_3$ is inactive, and in the combination $K_4$, e.g., the transmission channel $S_1$ is inactive, while the further channels $S_2, S_3, S_4$ are respectively switched to be active. That is to say, all established combinations in each case contain a plurality of active transmission channels and one inactive transmission channel. Each one of the combination leads to the creation of a respectively assigned relative $B_1$-map. By way of example, for the combination $K_1$, a relative $B_1$-map $BR_1$ is established, while the relative $B_1$-maps $BR_2, BR_3, BR_4$ are established for the combinations $K_2, K_3, K_4$.

As already explained with respect to FIG. 2, the radiofrequency pulse is selected in such a way that the spatial sensitivity of the transmission channels may in each case be established as a linear superposition of the transmission power of a plurality of transmission channels $S_1, S_2, S_3, S_4$. This relates to a linear combination of transmission channels $S_1, S_2, S_3, S_4$ as set forth at the outset. By way of example, this is provided in the aforementioned "low flip angle regime". The use of a plurality of transmission channels $S_1, S_2, S_3, S_4$ for generating a $B_1$-map, in particular for establishing the relative $B_1$-maps, offers the advantage that transmission power may be applied simultaneously to large parts of the measurement space and, in particular, to the entire field of view, which, for example, may not be provided for all examination objects in the case of only one active transmission antenna element or one activated transmission channel $S_1, S_2, S_3, S_4$.

In one embodiment, it may be possible, as plotted in FIG. 3 by a dashed line, for the combination K', (in which all transmission channels $S_1, S_2, S_3, S_4$ are active), to be used in place of one of the combinations $K_1$ to $K_4$. Therefore, the $B_1$-map generation module is able to carry out an exact back-calculation in relation to what proportion of the spatial sensitivity is due to the respective transmission channel $S_1$, $S_2$, $S_3$, $S_4$. Alternatively, this information may also only be established by the $B_1$-map normalization module 33. In order to be able to use these relative $B_1$-maps $BR_1$, $BR_2$, $BR_3$, $BR_4$, generated thus, in an actuation sequence optimization method, an exact quantification of the $B_1$-maps, e.g., the creation of at least one quantitative $B_1$-map, still is necessary. In the exemplary embodiment, merely a single quantitative $B_1$-map BQ is established for a slice, which is used for creating the four normalized $B_1$-maps. In the depicted example, this is brought about with the aid of the combination of transmission channels KQ. The combination KQ includes the active transmission channels $S_1$, $S_2$, $S_3$, $S_4$; e.g., all transmission channels of the magnetic resonance imaging system are used simultaneously. If, as indicated by the alternative K', one of the relative $B_1$-maps is established by the same combination of transmission channels that is also used to establish the quantitative $B_1$-map, to be precise in such a way that information about the transmission power or spatial sensitivity is available for all transmission channels $S_1$, $S_2$, $S_3$, $S_4$, it is possible to dispense with the acquisition of radiofrequency measurement values for establishing further quantitative $B_1$-maps.

That is to say, with the aid of the established relative $B_1$-maps $BR_1, \ldots, BR_4$ and the quantitative $B_1$-map BQ, it is possible to create four normalized $B_1$-maps, which each reproduce the spatial sensitivity of one of the transmission channels $S_1$, $S_2$, $S_3$, $S_4$ of the magnetic resonance imaging system in a dedicated manner or which permit the back-calculation of the sensitivity of one of the transmission channels $S_1$, $S_2$, $S_3$, $S_4$ in a dedicated manner. The normalized $B_1$-maps may then be used to create the radiofrequency pulse train in an optimization method for establishing an actuation sequence.

The procedure for a possible method for establishing a magnetic resonance system actuation sequence AS is explained in the following text using a simple example on the basis of the flowchart in accordance with FIG. 4.

Initially, in act 4.I, the various parameters that are used within the further method are predefined or imported. Within the scope of the present embodiments, by way of example, quantitative $B_1$-maps BQ for an individual slice and relative $B_1$-maps BR for this slice are imported in act 4.Ia.

Act 4.Ia progresses within the "$B_1$-map framework." Alternatively, it is also possible for quantitative $B_1$-maps and relative $B_1$-maps to be imported for a plurality of, in particular for all, slices to be acquired. In act 4.Ib, it is possible, if necessary, to also import $B_0$-maps B0 for the slices to be acquired.

System-specific parameters SP, such as the number of transmission channels, a maximum slew rate, a maximum gradient amplitude, etc., are imported in act 4.Ic and various examination-specific parameters, such as the positioning of the slices SL to be recorded, the sequence type ST etc., are imported in act 4.Id. Moreover, a desired target magnetization m is predetermined in act 4.Ie.

Finally, an exact k-space trajectory or a k-space trajectory type kTT is predetermined in act 4.If. This relates, for example, to whether this is a straight-line trajectory, a spiral trajectory, a radial trajectory, etc. This is because the individual RF pulse trains, e.g., the RF trajectories, for the individual transmission channels may be established over time as a function of a fixed "k-space trajectory," which may be predefined by a measurement protocol or individually from a user, in an optimization method for generating the actuation sequence AS. The "transmission k-space trajectory" (abbreviated to "trajectory" only in the following text) refers to the locations driven to in k-space at specific times by setting the individual gradients. The k-space is the spatial frequency space, and the trajectory in the k-space describes on which path the k-space is passed through in time when emitting an RF pulse by appropriate switching of the gradient pulses. Thus, by setting the k-space trajectory, it is possible to determine the spatial frequencies at which specific RF energy amounts are deposited. If only one k-space trajectory type kTT is predefined by the user or the measurement protocol, an optimized k-space trajectory may be calculated in the method.

The sequencing or order of the acts 4.Ia to 4.If is arbitrary.

Figure 4:
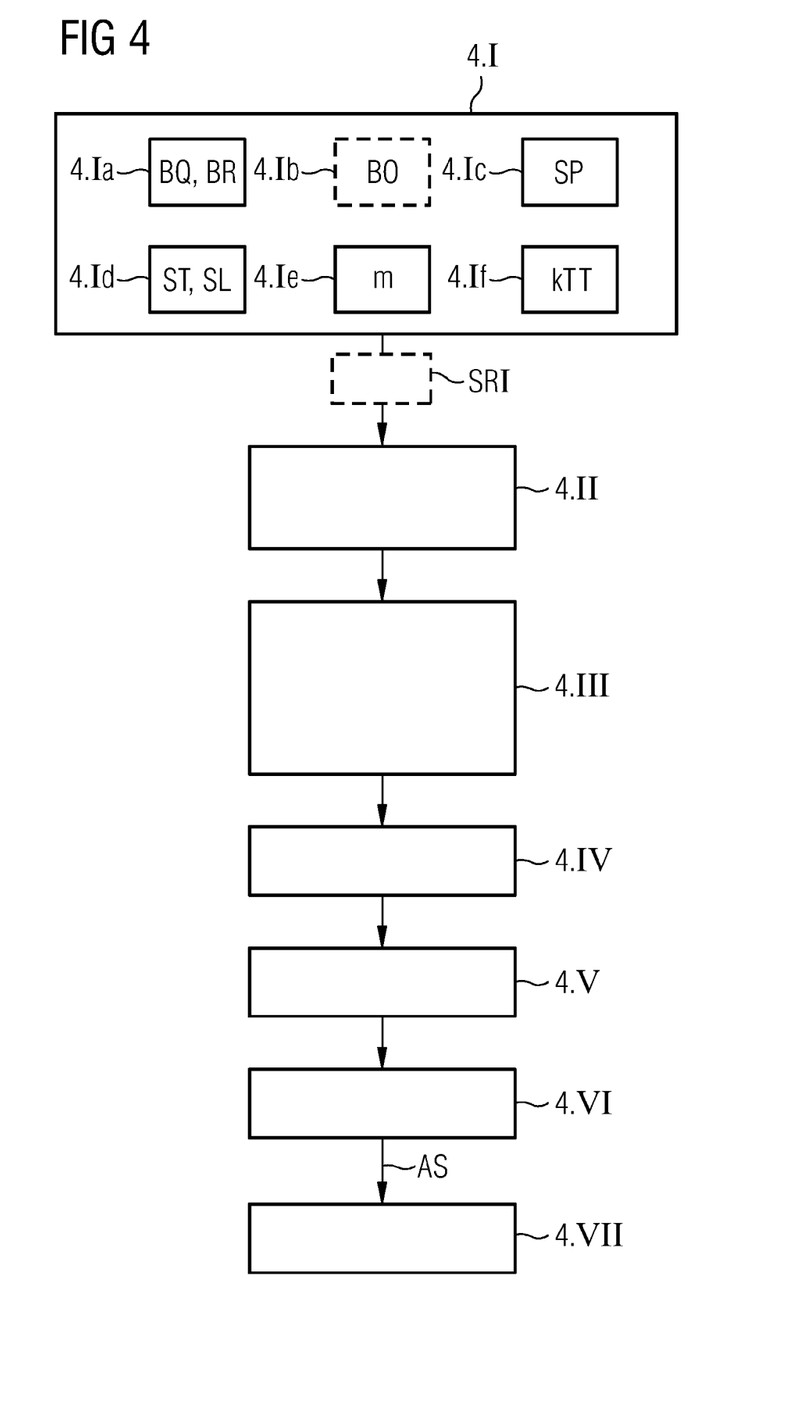
FIG. 4 depicts an exemplary embodiment of a method for establishing an actuation sequence.

FIG. 4 furthermore depicts the act SRI, in which the method for establishing the magnetic resonance system actuation sequence AS may be modified in order to operate in the manner. The relative $B_1$-maps BR, recalled from the memory module in act 4.Ib, and the transmitted quantitative $B_1$-maps BQ may be used to establish normalized $B_1$-maps. As explained in relation to FIG. 2, it is likewise possible to check in act SRI as to whether the normalized $B_1$-maps may be created in accordance with a predetermined quality criterion such that, (as likewise described in respect of FIG. 2), a renewed establishment and import of the relative $B_1$-maps may be triggered if necessary.

Then, an optimized k-space trajectory may be established in act 4.II provided that the k-space trajectory was not set in advance. There are various possibilities in this respect. By way of example, a suitable procedure is described in the patent application DE 10 2010 013 672 A1.

Then, the radiofrequency pulse train, in this case a multi-channel pulse train, is automatically designed in act 4.III. Here, the individual RF pulse sequences for the various transmission channels are expanded, e.g., an exact calculation is carried out in respect of which RF pulse form needs to be transmitted on which channel. This is initially brought about for a so-called "low flip range" or "low flip angle regime" with flip angles below 10°, since the magnetization property still is linear in this range. Here, an iterative optimization process is applied. Specifically, the so-called "conjugate gradient process" (CG method; conjugate gradients or else method of conjugate gradients) is used here. Then, the optimization takes place as described in, e.g., DE 10 2010 013 672 A1. However, in principle, other optimization methods, even non-iterative ones, may also be used.

The multi-channel pulse sequence obtained for the low flip range and available at the end of the optimization act 4.III may then be up-scaled in the act IV in order to achieve the actually desired target magnetization that may not lie in a flip angle range of less than 10°, but reaches up to a 90° flip angle. This is brought about by multiplying the amplitudes of the individual pulses by the desired scaling factor.

The error, which may occur during up-scaling, is corrected in act 4.V by a partial Bloch simulation. Such a partial Bloch simulation is only carried out at individual times within the pulse sequence. Here, with application of the Bloch equations, the data for the respective time, at which the check may take place, are tested in a simulator with application of the Bloch equations and the magnetization achieved thus is calculated. It is possible to discover deviations from the prescriptions of the target magnetization and appropriate, relatively small corrections may be undertaken by changing the radiofrequency pulse sequences.

Subsequently, all found parameters are once again tested in act 4.VI by a time-complete Bloch simulation. In the process, a test is carried out as to whether the magnetization that is achieved with the parameters in actual fact corresponds to the target magnetization.

The actuation sequence AS is transferred for buffer storage or immediate execution in act VII.

The above-described makes clear that the embodiments provide effective options for accelerating a method for establishing $B_1$-maps and/or an actuation sequence in an effective manner.

Here, reference is made to the fact that the features of all exemplary embodiments or developments disclosed in the figures may be used in any combination. Finally, reference is likewise made to the fact that the methods, described above in detail, for establishing $B_1$-maps, for establishing an actuation sequence for a magnetic resonance imaging system and for operating a magnetic resonance imaging system, and the actuation sequence establishment system, the $B_1$-map establishment system and magnetic resonance system are merely exemplary embodiments, which may be modified by a person skilled in the art in varied ways without departing from the scope of the embodiments. Furthermore, the terms "module" or "unit" do not preclude the possibility of the relevant components including a plurality of partial components that, optionally, may also be arranged distributed in space. Furthermore, the use of the indefinite article "a" or "an" does not preclude the possibility of the relevant features also being present a number of times.

The above-described method may be implemented via a computer program product including one or more readable storage media having stored thereon instructions executable by one or more processors of the computing system. Execution of the instructions causes the computing system to perform operations corresponding with the acts of the method described above.

The instructions for implementing processes or methods described herein may be provided on non-transitory computer-readable storage media or memories, such as a cache, buffer, RAM, FLASH, removable media, hard drive, or other computer readable storage media. A processor performs or executes the instructions to train and/or apply a trained model for controlling a system. Computer readable storage media include various types of volatile and nonvolatile storage media. The functions, acts, or tasks illustrated in the figures or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Likewise, processing strategies may include multiprocessing, multitasking, parallel processing and the like.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for establishing $B_1$-maps for establishing an actuation sequence for a magnetic resonance imaging system comprising a number of transmission channels used for generating a radiofrequency field for magnetic resonance excitation of an examination object, the method comprising:
   emitting a first radiofrequency field using a first transmission channel;
   acquiring first radiofrequency field measurement values for the emitted first radiofrequency field;
   creating a first relative $B_1$-map based on the first radiofrequency field measurement values from the first transmission channel;
   emitting a further radiofrequency field using a further transmission channel;
   acquiring further radiofrequency field measurement values for the emitted further radiofrequency field of the further transmission channel;
   creating an additional relative $B_1$-map based on the further radiofrequency field measurement values from the further transmission channel;
   repeating, for a number of transmission channels, the emitting of a further radiofrequency field, the acquiring of further radiofrequency field measurement values, and the creating an additional relative $B_1$-map; and
   storing the generated relative $B_1$-maps for multiple use.

2. The method as claimed in claim 1, further comprising:
   establishing a quantitative $B_1$-map;
   establishing normalized $B_1$-maps based on the relative $B_1$-maps and the quantitative $B_1$-map; and
   establishing an actuation sequence for acquiring magnetic resonance measurement data using the normalized $B_1$-maps.

3. The method as claimed in claim 2, wherein a number of generated relative $B_1$-maps corresponds at least to a number of transmission channels for generating a radiofrequency field in a measurement space of the magnetic resonance imaging system used for acquiring raw magnetic resonance data.

4. The method as claimed in claim 2, further comprising:
   establishing a further quantitative $B_1$-map;
   establishing further normalized $B_1$-maps based on the stored relative $B_1$-maps and the further quantitative $B_1$-map; and
   establishing a further actuation sequence for acquiring further magnetic resonance measurement data using the further normalized $B_1$-maps.

5. The method as claimed in claim 4, wherein a number of generated relative $B_1$-maps corresponds at least to a number of transmission channels for generating a radiofrequency field in a measurement space of the magnetic resonance imaging system used for acquiring raw magnetic resonance data.

6. The method as claimed in claim 4, wherein the quantitative $B_1$-map, the further quantitative $B_1$-map, or the quantitative $B_1$-map and the further quantitative $B_1$-map are generated using a combination of a plurality of transmission channels of the magnetic resonance imaging system.

7. The method as claimed in claim 2, wherein at least one relative $B_1$-map is generated using a combination of a plurality of transmission channels of the magnetic resonance imaging system.

8. The method as claimed in claim 7, wherein the quantitative $B_1$-map, the further quantitative $B_1$-map, or the quantitative $B_1$-map and the further quantitative $B_1$-map are generated using a combination of the plurality of transmission channels of the magnetic resonance imaging system.

9. The method as claimed claim 8, wherein at least two transmission channels of a combination of transmission channels used for generating the quantitative $B_1$-map are contained in a combination of transmission channels used for generating at least one of the relative $B_1$-maps.

10. The method as claimed in claim 7, wherein each relative $B_1$-map of the number of relative $B_1$-maps is generated using a combination of the plurality of transmission channels of the magnetic resonance imaging system.

11. The method as claimed in claim 10, wherein the quantitative $B_1$-map, the further quantitative $B_1$-map, or the quantitative $B_1$-map and the further quantitative $B_1$-map are generated using a combination of the plurality of transmission channels of the magnetic resonance imaging system.

12. The method as claimed claim 11, wherein at least two transmission channels of a combination of transmission channels used for generating the quantitative $B_1$-map are contained in a combination of transmission channels used for generating at least one of the relative $B_1$-maps.

13. The method as claimed in claim 2, wherein the quantitative $B_1$-map is determined taking into account a predetermined quality criterion, wherein the predetermined quality criterion is a spatial resolution, a measurement error when determining the qualitative B1-map, or the spatial resolution and the measurement error when determining the quantitative $B_1$-map.

14. The method as claimed in claim 2, wherein there is a comparison between a quality criterion for relative $B_1$-maps and a quality criterion for quantitative $B_1$-maps, wherein the number of relative $B_1$-maps is established based on the comparison.

15. A method for operating a magnetic resonance system, the method comprising:
establishing an actuation sequence for a magnetic resonance imaging system comprising:
(1) establishing a number of relative $B_1$-maps comprising:
emitting a first radiofrequency field using a first transmission channel;
acquiring first radiofrequency field measurement values for the emitted first radiofrequency field;
creating a first relative $B_1$-map based on the first radiofrequency field measurement values from the first transmission channel;
emitting a further radiofrequency field using a further transmission channel;
acquiring further radiofrequency field measurement values for the emitted further radiofrequency field of the further transmission channel;
creating an additional relative $B_1$-map based on the further radiofrequency field measurement values from the further transmission channel;
repeating, for a number of transmission channels, the emitting of a further radiofrequency field, the acquiring of further radiofrequency field measurement values, and the creating an additional relative $B_1$-map; and
storing the generated relative $B_1$-maps for multiple use;
(2) establishing a quantitative $B_1$-map;
(3) establishing normalized $B_1$-maps based on the relative $B_1$-maps and the quantitative $B_1$-map; and
(4) establishing an actuation sequence for acquiring magnetic resonance measurement data using the normalized $B_1$-maps; and
operating the magnetic resonance system using the actuation sequence.

16. A $B_1$-map establishment system comprising:
an input interface configured to acquire first radiofrequency field measurement values;
a $B_1$-map establishment module configured to establish a first quantitative $B_1$-map based on the first radiofrequency field measurement values;
a memory module configured to repeatedly recall relative $B_1$-maps from a memory module; and
a $B_1$-map normalization module configured to establish a number of normalized first $B_1$-maps using the relative first $B_1$-maps recalled from the memory module and the first quantitative $B_1$-map.

17. The $B_1$-map establishment system as claimed in claim 16, further comprising:
a quality criterion interface configured to predetermine a quality criterion.

18. An actuation sequence establishment system comprising:
a $B_1$-map establishment system comprising:
an input interface configured to acquire first radiofrequency field measurement values;
a $B_1$-map establishment module configured to establish a first quantitative $B_1$-map based on the first radiofrequency field measurement values;
a memory module configured to repeatedly recall relative $B_1$-maps from a memory module; and
a $B_1$-map normalization module configured to establish a number of normalized first $B_1$-maps using the relative first $B_1$-maps recalled from the memory module and the first quantitative $B_1$-map; and
a sequence establishment unit configured to establish an actuation sequence for acquiring magnetic resonance measurement data using the normalized first $B_1$-maps, normalized second $B_1$-maps, or the normalized first $B_1$-maps and the normalized second $B_1$-maps,
wherein the normalized second $B_1$-maps are established from the $B_1$-map normalization module using the relative first $B_1$-maps recalled from the memory module and a second quantitative $B_1$-map.

19. The system as claimed in claim 18, further comprising:
a quality criterion interface configured to predetermine a quality criterion.

20. An apparatus comprising:
at least one processor; and
at least one memory including computer program code for one or more programs; the at least one memory and the computer program code configured to, with the at least one processor, cause the apparatus to at least perform:
emit a first radiofrequency field using a first transmission channel;
acquire first radiofrequency field measurement values for the emitted first radiofrequency field;
create a first relative $B_1$-map based on the first radiofrequency field measurement values from the first transmission channel;
emit a further radiofrequency field using a further transmission channel;
acquire further radiofrequency field measurement values for the emitted further radiofrequency field of the further transmission channel;

create an additional relative $B_1$-map based on the further radiofrequency field measurement values from the further transmission channel;
repeat, for a number of transmission channels, the emitting of a further radiofrequency field, the acquiring of further radiofrequency field measurement values, and the creating an additional relative $B_1$-map; and
store the generated relative $B_1$-maps for multiple use.

* * * * *